(12) United States Patent
Lin et al.

(10) Patent No.: US 9,789,141 B2
(45) Date of Patent: Oct. 17, 2017

(54) PROBIOTIC ENHANCEMENT OF STEROID AND IMMUNE SUPPRESSOR ACTIVITY IN MAMMALS WITH CHRONIC DISEASES

(71) Applicant: IMAGILIN TECHNOLOGY, LLC, Frederick, MD (US)

(72) Inventors: Jhy-Jhu Lin, Frederick, MD (US); Gen Kato, Tokyo (JP); Takuo Ishida, Tokyo (JP)

(73) Assignee: IMAGILIN TECHNOLOGY, LLC, Frederick, MD (US)

( * ) Notice: Subject to any disclaimer, the term of this patent is extended or adjusted under 35 U.S.C. 154(b) by 0 days.

(21) Appl. No.: 15/148,609

(22) Filed: May 6, 2016

(65) Prior Publication Data

US 2016/0243173 A1    Aug. 25, 2016

Related U.S. Application Data

(63) Continuation of application No. 12/806,392, filed on Aug. 11, 2010, now Pat. No. 9,364,507.

(60) Provisional application No. 61/273,895, filed on Aug. 11, 2009.

(51) Int. Cl.
    *A61K 35/74* (2015.01)
    *A61K 35/741* (2015.01)
    *A61K 35/744* (2015.01)
    *A61K 36/064* (2006.01)

(52) U.S. Cl.
    CPC ............ *A61K 35/744* (2013.01); *A61K 35/74* (2013.01); *A61K 36/064* (2013.01)

(58) Field of Classification Search
    None
    See application file for complete search history.

(56) References Cited

U.S. PATENT DOCUMENTS

| | | | | |
|---|---|---|---|---|
| 5,561,138 | A | 10/1996 | Armstrong | 514/291 |
| 7,935,334 | B2 | 5/2011 | Lin | 424/537 |
| 2004/0141925 | A1 | 7/2004 | Bosch et al. | 424/46 |
| 2006/0073130 | A1 | 4/2006 | Farmer et al. | 424/93.46 |
| 2006/0111272 | A1 | 5/2006 | Roberts et al. | 514/2 |
| 2007/0020328 | A1 | 1/2007 | Lin | 424/456 |
| 2010/0209527 | A1 | 8/2010 | Sato et al. | 424/537 |

FOREIGN PATENT DOCUMENTS

| | | |
|---|---|---|
| WO | WO 2009128930 A1 | 10/2009 |
| WO | WO 2011047153 A1 | 4/2011 |

OTHER PUBLICATIONS

Schwartz et al. 2008 (Optimizing Conventional Therapy for Inflammatory Bowel Disease; Current Gastroenterology Reports 10:585-590).*
Kohn et al. 2006 (Primary Immune-Mediated Hemolytic Anemia in 19 cats: Diagnosis, Therapy, and Outcome; J Vet Intern Med 20:159-166).
Ray et al. 2000 (Chapter 19: Pediocin, see p. 525, 526, 535, etc. in Natural Food Antimicrobial Systems; ed. A. S. Naidu).
Dacie et al. 2001 (Historical Review: The immune haemolytic anaemias: a century of exciting process in understanding; British Journal of Haematology, 2001, 114, 770-785).
Dacie et al. 2001 British Journal of Haematology, 114: 770-785.
Czeruka et al. 2007 (Review article: yeast as probiotics—*Saccharomyces boulardii*; Alimentary Pharmacology & Therapeutics, 26(6): 767-778; see p. 770).
Hartmann et al. 1998 (Natural steroids in food, Food Chemistry 62(1): 7-20; see p. 9 and Table 1).
Golden et al. 2008 (Clinical indications for probiotics: An overview; CID 2008:46, Supplement 2, pp. S96-S100).
Fagiolo et al. 1994 (Hight cytokine serum levels in patients with autoimmune hemolytic anemia (AIHA); Immunol. Invest. 23(6-7): 449-56).
ExList Patent Information Sheet—Prednisolene; downloaded 2013; WebMD LLC; http://www.rxlist.com/script/main/hp.asp.
ExList Patent Information Sheet—Azathioprine; downloaded 2013; WebMD LLC; http://www.rxlist.com/script/main/hp.asp.
Sissions 1989 (Potential of Probiotic Organisms to Prevent Diarrhoea and Promote Digestion in Farm Animals—A Review; J. Sci. Food Agric 49; 1-13).

* cited by examiner

*Primary Examiner* — Gary Nickol
*Assistant Examiner* — Mary Lyons
(74) *Attorney, Agent, or Firm* — Stein IP, LLC (57) ABSTRACT

This invention relates to use of probiotics, particularly *P acidilactici* and *S boulardii*, for use in conjunction with steroids and other immune suppressor agents to ameliorate symptoms of autoimmune diseases, especially disease symptoms arising from the body's production of antibodies against autologous blood cells. The practice of the invention sustains ameliorative response associated with immune suppressor agents while lowering the amount of immune suppressor agents required for treatment.

12 Claims, 4 Drawing Sheets

PROBIOTIC ENHANCEMENT OF STEROID AND IMMUNE SUPPRESSOR ACTIVITY IN MAMMALS WITH CHRONIC DISEASES

CROSS-REFERENCE TO RELATED APPLICATIONS

This application is a continuation of U.S. application Ser. No. 12/806,392, filed Aug. 11, 2010, now allowed, which claims the benefit of Provisional Application No. 61/273,895, filed Aug. 11, 2009, in the U.S. Patent Office All disclosures of the documents named above are incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable

BACKGROUND OF THE INVENTION

1. Field of the Invention

The invention relates to methods for treating mammals with chronic diseases.

2. Description of Related Art Including Information Disclosed Under 37 CFR 1.97 and 1.98.

Autoimmune diseases are related to the disruption of host immune systems. Chronic autoimmune diseases, such as autoimmune hemolytic anemia (henceforth AIHA), immune-mediated hemolytic anemia (henceforth IMHA), inflammatory bowel disease (henceforth IBD), and atopic dermatitis (henceforth AD), typically require consistent treatment with anti-inflammatory drugs such as corticosteroids and immune suppressors such as cyclosporine and azathioprine.

Long term application of these drugs can cause significant drug side effects. As soon as the symptoms are under control, medical doctors and veterinarians often try to reduce dosages or to eliminate entirely the use of these drugs. Unfortunately, the remission of disease makes this approach very challenging. This has created a demand for therapeutics comprised of natural materials with few or no side effects to treat these chronic autoimmune diseases or to reduce the side effects of anti-inflammatory drugs and immune suppressors.

AIHA in humans and IMHA in canines and felines, is an immune disorder caused by antibodies directed against unmodified autologous red cells. AIHA is an increasingly recognized complication of anti-neoplastic therapy in cancer patients, in particular those with chronic lymphocytic leukemia (henceforth CLL). In addition, AIHA is quite often seen in patients with infectious diseases, sometimes in "collagen disorders' which are systemic autoimmune disorders, and sometimes after organ transplantation. These disorders are acute or chronic diseases.

Inflammatory bowel disease (henceforth IBD) is a general term to describe chronic intestinal inflammation, in which inflammatory cells have spread to the gastrointestinal (henceforth GI) tract. Depending on location and nature of the inflammatory changes, IBD can be classified into two major types—Crohn's disease and ulcerative colitis. Crohn's disease can affect any part of the GI tract with a majority of the cases starting in the ileum. Ulcerative colitis is restricted to the colon and rectum. IBD is considered to be the most probable cause of chronic vomiting and diarrhea in cats (Omi et al., 2008). It is well established that intestinal microflora play an important role in the pathogenesis of IBD (Heilpern and Szilagyi, 2008; Kanauchi et al., 2009). The intestinal microflora is a large bacterial community that colonizes the gut and which affects the physiology and pathology of the host's mucosal immune system (Mamaskos and Kolios, 2008).

The skin is the largest immunologic organ by area and is affected by both external and internal factors, as well as innate and adaptive immune responses. Many skin disorders, such as atopic dermatitis (henceforth AD) are immune mediated. Most of dermatologic diseases are chronic, inflammatory, and proliferative (Fonaciet et al., 2010). Steroids are often used as the first-line treatment of AD, and have been shown to be very effective in improving the symptoms; however, steroids can also cause severe side effects. Other medications such as cyclosporine have been shown to be effective in treating severe AD, and may be used as a substitute for steroids. However, the complications of side effects associated with long-term application can be serious (Haw et al., 2010).

Animals and humans suffering from AD, IBD, AIHA, and IMHA have disruptions of their immune systems and often require long-term steroid and/or immuno-suppressor treatment. A great deal of emphasis has been placed on reducing and alleviating the many severe side effects that these powerful treatments can cause.

The standard treatment in dogs and cats with chronic digestive disorders such as IBD or nonspecific enteropathies (henceforth NPE) is feeding a nutritionally balanced, highly digestible elimination diet. Alternatively, long term administration of multiple drugs, including digestive drugs, antibiotics, immune suppressors, and inflammation suppressors to cats and dogs have been adapted. However, long term, multi-drug regimens cause severe side effects to dogs, cats and humans (Jergens, 1999, Allenspach et al., 2006). It is desirable to reduce the number of drugs used in treatment as soon as symptoms are reduced and the patient is stable. Similar multiple drugs are used in treatment of dogs suffering from chronic diseases such as IMHA (Grundy and Barton, 2001) and such skin diseases as AD. Unfortunately, the recurrence of symptoms is often observed when the amounts of drugs are reduced, especially in the case of reducing corticosteroids such a prednisolone.

Probiotics are beneficial microorganisms that naturally exist in the GI tracts of humans and animals. Oral administration of adequate amounts of probiotics reestablishes the micro-ecosystsms in GI tracts and have been shown to alleviate antibiotic-induced diarrhea (Kaur et al., 2009). Among different probiotics, *Pediococcus adidilactici* is reported to have better resistance against high temperatures, oxygen exposure, and stomach acid environments than other probiotics (Lin, 2006, Lin and Ishida, 2008). Enhanced immune responses in broiler chicken and rats were noted when the animals were given *P. acidilactici* alone or in a combination of *P. acidilactici* and *Saccharomyces boulardii* (Lee et al., 2007). *S. boulardii* was also described to enhance immune responses against *Clostridium difficle* toxin A (Owner et al., 2001). Rats fed with *P. acidilactici* and *S. boulardii* had both B-cells and T-cells significantly increased (Lin and Ishida, 2009). When high amounts of live *P. acidilactici* were administered with antibiotics, substantial numbers of live *P. acidilactici* were able to survive even under antibiotic treatment. Therefore, administering *P. acidilactici* and *S. boulardii* together with antibiotics or other drugs can be a routine treatment for dogs and cats suffering from digestive disorders (Mitztani et al., 2007, Lin and Ishida, 2008).

The use of probiotics as alternative medicines against infectious diseases has been disclosed in U.S. patent application Ser. No. 11/493,859, incorporated herein by reference.

The effects of probiotics on human and animals under environmental or biological changes have been disclosed in U.S. patent application Ser. No. 12/386,285, incorporated herein by reference.

Embodiments of the present application include methods for reducing symptoms in humans and pets such as dogs and cats affected with autoimmune symptoms such as AIHA, IMHA, IBD, NPD, or AD by treating with probiotics *P. acidilactici* and *S. boulardii*. Embodiments include methods for reducing the occurrences of IBD or NPD symptoms, AIHA or IMHA symptoms, and AD symptoms when the dosages of drugs are reduced.

The foregoing examples of the related art and limitations related therewith are intended to be illustrative and not exclusive. Other limitations of the related art will become apparent to those of skill in the art upon a reading of the specification and a study of the drawings.

BRIEF SUMMARY OF THE INVENTION

The following embodiments and aspects thereof are described and illustrated in conjunction with systems, tool and methods which are meant to be exemplary and illustrative, not limiting in scope. In various embodiments, one or more of the above—described problems have been reduced or eliminated, while other embodiments are directed to other improvements.

Embodiments include a method of treating autoimmune hemolytic anemia in mammals, including humans and pets requiring such treatment. That method comprises the steps of obtaining a probiotic preparation of living microorganisms, and administering an effective amount of the probiotic preparation to the human requiring treatment for autoimmune anemia.

Embodiments include a method for treating inflammatory bowel disease or nonspecific enteropathies disease or atopic dermatitis in mammals, including humans and pets requiring such treatment. That method comprises the steps, obtaining a probiotic preparation of living *Pediococcus acidilactici*, and administering an effective amount of the probiotic preparation to the mammal requiring treatment for inflammatory bowel disease or nonspecific enteropathies disease or atopic dermatitis.

Embodiments include a method of reducing side effects associated with steroid and immune suppressor treatment and reducing the dosage of steroids and immune suppressors required to treat autoimmune hemolytic anemia in mammals, including humans and pets requiring such treatment. The method comprises the steps, obtaining a probiotic preparation of living microorganisms, and administering an effective amount of the probiotic preparation to the mammal, including a human and a pet requiring treatment for autoimmune anemia who is being treated with steroids and immune suppressors.

Embodiments include a method of reducing side effects associated with steroid and immune suppressor treatment and reducing the dosage of steroids and immune suppressors required to treat inflammatory bowel disease or nonspecific enteropathies disease or atopic dermatitis in mammals, including humans and pets requiring such treatment. The method comprises the steps, obtaining a probiotic preparation of living *Pediococcus acidilactici* and *Saccharomyces boulardii*, and administering an effective amount of the probiotic preparation to the mammal, including a human and a pet with inflammatory bowel disease or nonspecific immunopathies disease or atopic dermatitis which is being treated with steroids and immune suppressors.

DETAILED DESCRIPTION OF THE INVENTION

In this disclosure, IBD means inflammatory bowel disease; NEP means nonspecific enteropathies disease; IMHA means immune-mediated hemolitic anemia, AIHA means autoimmune hemolytic anemia; GI means gastrointestinal; MMS means probiotics comprised of *P. acidilactici* and *S. boulardii* microorganisms; PCV means pack cell volume; EOD means every other day; AD means atopic dermatitis. IMHA Treatment.

AIHA in humans, and IMHA in canines and felines, is an immune disorder caused by antibodies directed against unmodified autologous red cells. The disorders are acute or chronic diseases.

The conventional therapy of warm antibody AIHA or IMHA is treatment with glucocorticosteroids with or without high doses of immunoglobins. After initial remission, the dose is tapered down slowly and with caution, and in some cases, low-dose maintenance therapy is required (Valent and Lechner, 2008). If the response to glucocorticosteroids is not adequate, the immune suppressor, cyclosporine A, is a reasonable choice for the treatment (Diehl and Fetchum, 1998). The side effects of long term drug applications remain a main concern.

Embodiments of the current disclosure involve administration of *P. acidilactici* and *S. boulardii* probiotics together with steroids and/or immune suppressors to cats and dogs suffering from the chronic diseases IMHA and IBD. Inclusion of probiotics along with steroids and/or immune suppressors was found to allow the use of reduced amounts of steroids and/or immune suppressors.

Example 1

Figure 1A:
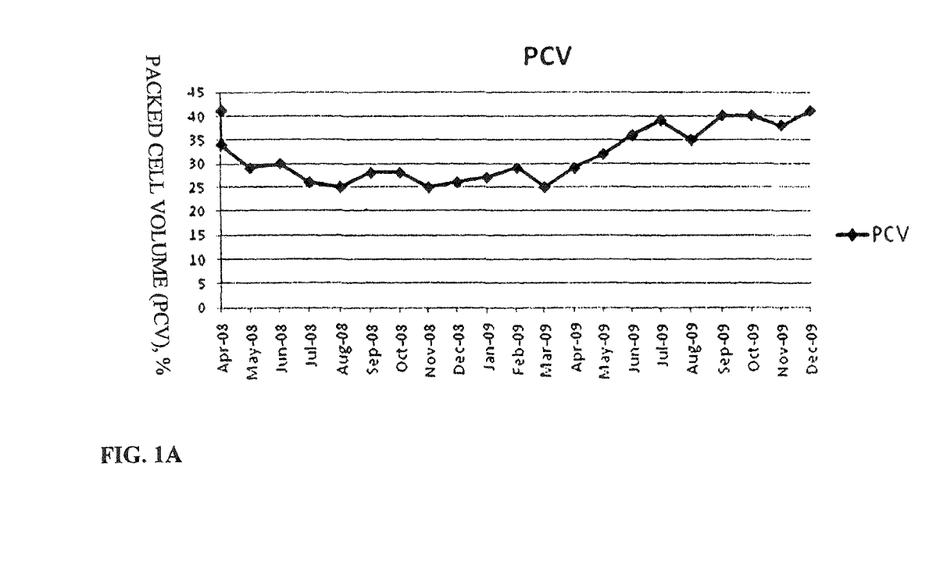
FIG. 1A shows the blood percent packed cell volume of a nine year old dog with IMHA during treatment with prednisolone, cyclosporine and probiotics *P. acidilactici* and *S. boulardii*.
Figure 1B:
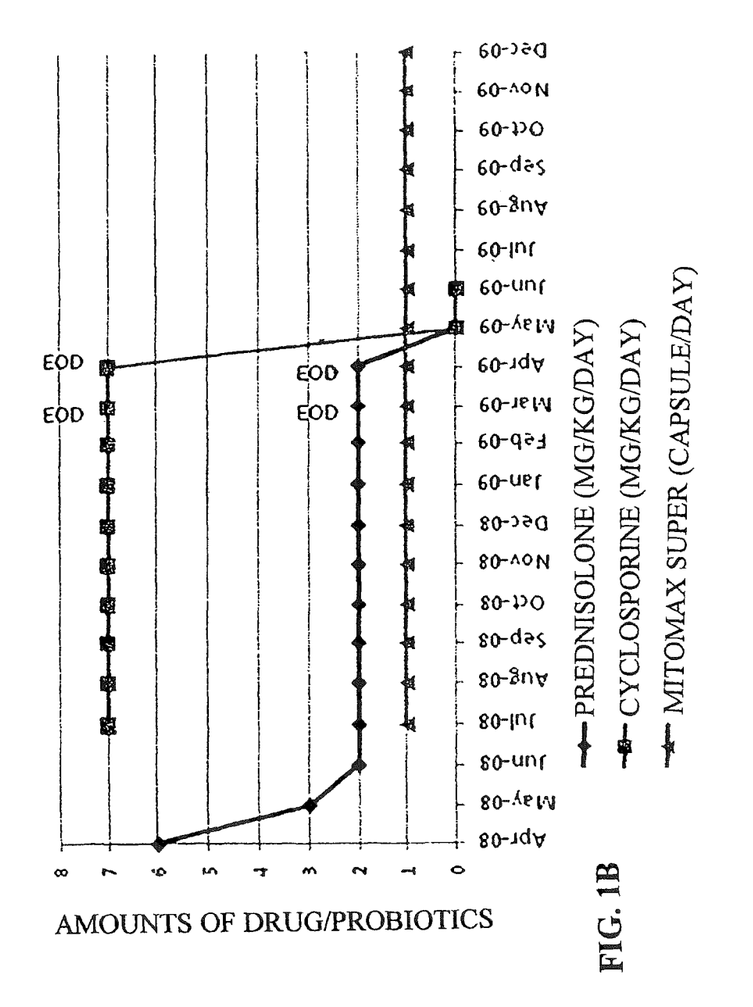
FIG. 1B shows the treatment of a nine year old dog with IMHA with prednisolone, cyclosporine and probiotics *P. acidilactici* and *S. boulardii*.

FIGS. 1A and 1B show the effects on PCV (low PCV as an indicator of IMHA) of treating a nine year old dog with IMHA with prednisolone followed by cyclosporine and probiotics *P. acidilactici* and *S. boulardii*.

FIG. 1A shows the PCV over a 20 month period from April 2008 to December 2009. After an abrupt drop at the beginning of the study, the PCV level began a substantial raise beginning March 2009, 11 months into the study.

FIG. 1B shows the daily treatments of the dog over the period in FIG. 1A. The steroid prednisolone was initially administered at 6 mg/kg/day, which was reduced to 3 mg/kg/day after one month, and to 2 mg/kg/day from months 2 to 11, when it was administered at 2 mg/kg/day every other day for one month when it was totally eliminated. Cyclosporine was administered at 7 mg/kg/day from the third month through the 11.sup.th month when the drug was administered at 7 mg/kg/day but administered every other day for one additional month, when it was eliminated at 12 months. The probiotic MITOMAXSUPER™ was administrated at one capsule-per day for the period from 3 months through the end of the study at 20 months. MITOMAXSUPER™ is a trademark owned by Imagilin Technologies, Frederick, Md. for a probiotic capsule containing 400 mg of a mixture of one billion live *P. acidilactici* and *S. boulardii* microorganisms.

Comparison of FIGS. 1A and 1B show that the decline in PCV associated with IMHA was stabilized by the combination treatment with prednisolone, cyclosporine and probiotic MITOMAXSUPER™. Reduction of administration of prednisolone and cyclosporine at month 11 and elimination at both drugs at month 12, while maintaining the dosage of probiotic throughout the study, resulted in a substantial restoration of the PCV with suppression of IMHA.

Example 2

Figure 2A:
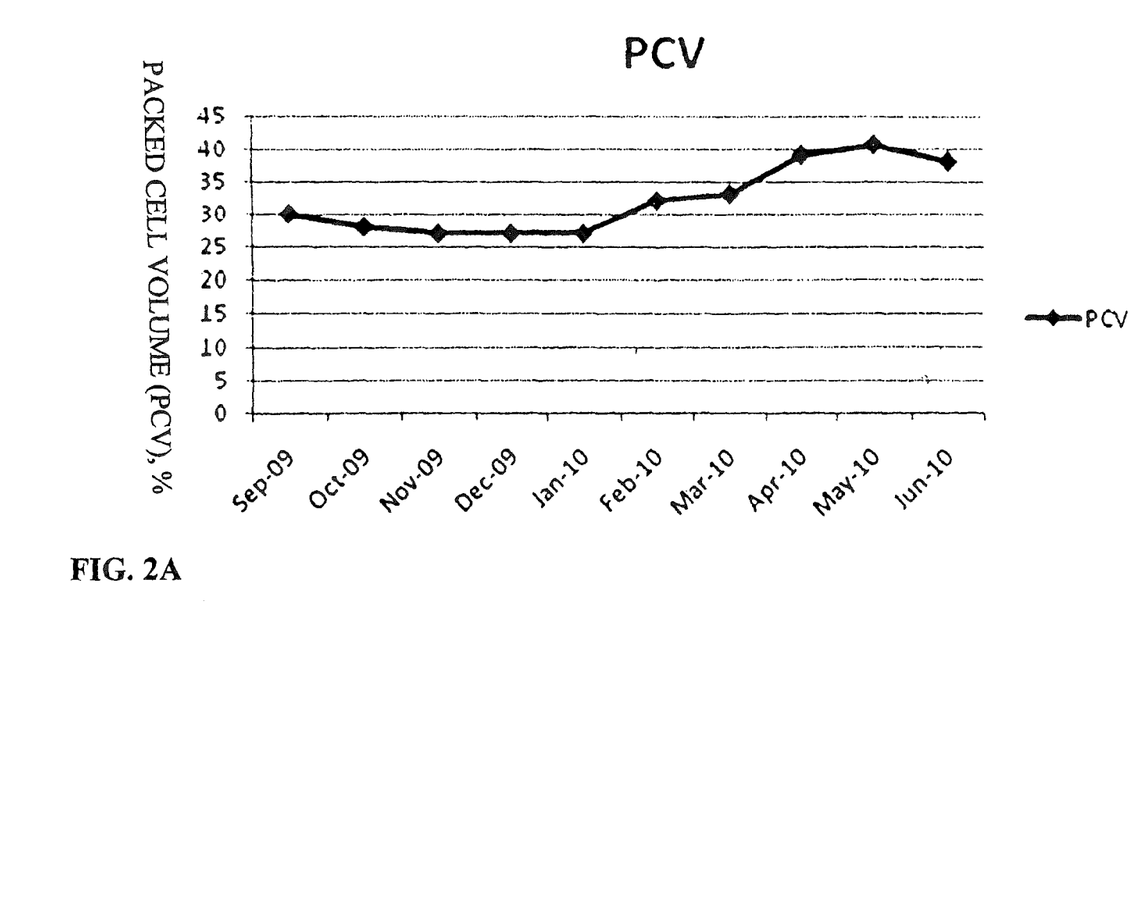
FIG. 2A shows the blood percent packed cell volume of a thirteen year old dog with IMHA during treatment with prednisolone, lefluomide and probiotics *P. acidilactici* and *S. boulardii*.
Figure 2B:
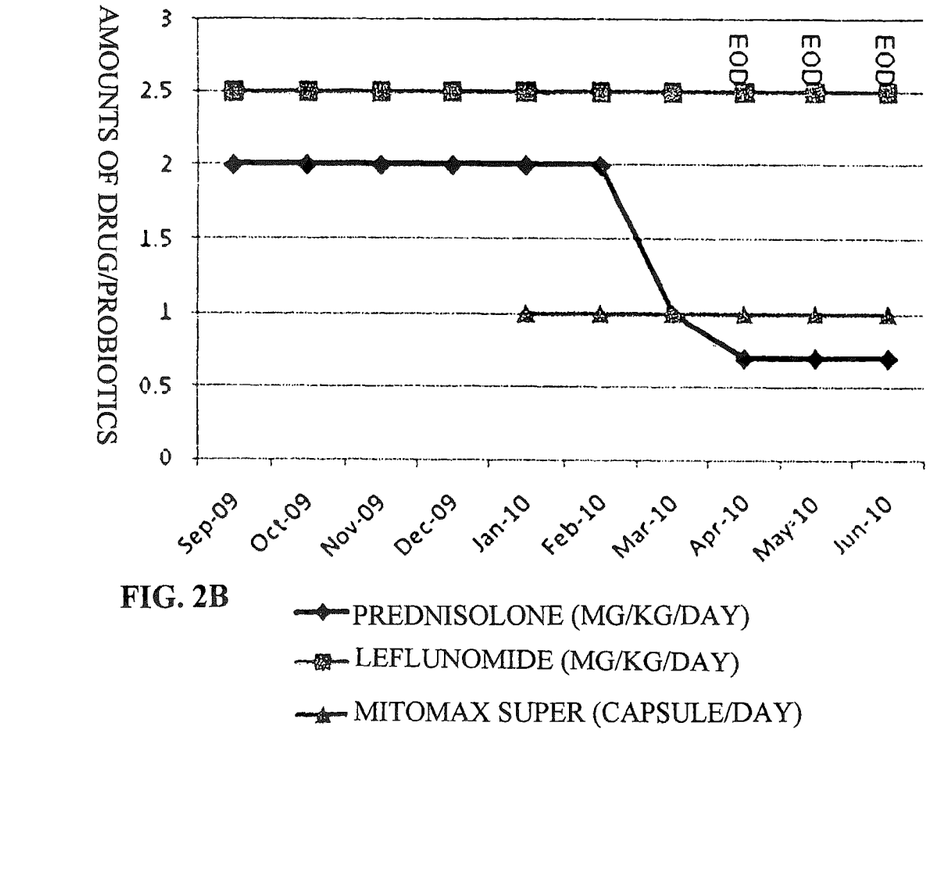
FIG. 2B shows the treatment of a thirteen year old dog with IMHA with prednisolone, lefluomide and probiotics *P. acidilactici* and *S. boulardii*.

FIGS. 2A and 2B show the effects on PCV (low PCV as an indicator of IMHA) of treating a thirteen year old Shihtzu dog with IMHA with prednisolone and leflunomide and probiotics *P. acidilactici* and *S. boulardii*.

FIG. 2A shows the PCV over a 9 month period from September 2009 to June 2010. After an abrupt drop at the beginning of the study, the PCV level began a substantial raise beginning January 2010, 5 months into the study.

FIG. 2B shows the daily treatments of the dog over the period in FIG. 2A. The steroid prednisolone was initially administered at 2 mg/kg/day, which was reduced to 1 mg/kg/day after 6 months, and to 0.75 mg/kg/day from months 8 to 9. Leflunomide was administered at 2.5 mg/kg/day from the beginning for 7 months when the drug was administered at 2.5 mg/kg/day but administered every other day for two additional month. The probiotic MITOMAXSUPER™ was administrated at one capsule, one billion live microorganisms, per day for the period from 4 months through the end of the study at 9 months.

Comparison of FIGS. 2A and 2B show that the decline in PCV associated with IMHA was stabilized by the combination treatment with prednisolone and leflunomide. The probiotic MITOMAXSUPER™ was added one month before reduction and prednisolone and leflunomide and probiotic therapy was continued to the end of the study. Reduction of administration of prednisolone and cyclosporine while maintaining the level of probiotic resulted in restoration of the PCV and concomitant suppression of IMHA.

Example 3

TABLE 1

Effects of MITOMAXSUPER ™ on drug treatment of dogs with IMHA

| Pets | Diseases[1] | Drugs treatment | Drugs dosage reduction after feeding with probiotics[2] | Symptom Improvement (% PCV increase[4]) |
|---|---|---|---|---|
| 9 year old, spayed, Miniature Schnauzer | IMHA | Prednisolone, Cyclosporine | Prednisolone reduced from 2 mg/kg/day to 2 mg/kg/EOD after 9 months, eliminated after 11 months; Cyclosporine reduced from 7 mg/kg/day to 7 mg/kg/EOD after 9 months, and eliminated after 11 months | from 25% to 40% |
| 4 year and 4 month, spayed Chiwawa | IMHA | Prednisolone, Azathioprine | Prednisolone reduced from 4 mg/kg/day to 1 mg/kg/day after 2 months | from 20% to 42% |
| 9 years and 1 month old, spayed, Welsh Corgi | IMHA | Prednisolone, Azathioprine | [3]Prednisolone reduced from 4 mg/kg/day to 3 mg/kg/day after 9 days, reduced to 2.5 mg/kg/day after 25 days | from 17% to 34% |
| 13 year and 6 month old, spayed, Miniature Dachshund | IMHA | Prednisolone, Azathioprine | Prednisolone reduced from 4 mg/kg/day to 3 mg/kg/day within a month | from 15% to 25% |
| 13 years old Shintzu | IMHA | Prednisolone, Leflunomide | Prednisolone reduced from 2 mg/kg/day to 1 mg/kg/day after 3 months, to 0.7 mg/kg/day after 4 months; Lefluomide reduced from 2.5 mg/kg/day to 2.5 mg/kg/EOD after 4 months | from 26% to 38% |
| 8 years old, Shihtzu | IMHA | Prednisolone, Azathioprine | Prednisolone reduced from 2 mg/kg to 0.5 mg/kg after 2 months, to 0.3 mg/kg/day after 3 months; Azathioprine 2 mg/kg/day was eliminated after 5 months | from 34% to 40% |

TABLE 1-continued

Effects of MITOMAXSUPER ™ on drug treatment of dogs with IMHA

| Pets | Diseases[1] | Drugs treatment | Drugs dosage reduction after feeding with probiotics[2] | Symptom Improvement (% PCV increase[4]) |
|---|---|---|---|---|
| 10 years old female, Pomeranian | IMHA | Prednisolone, Azathioprine | Prednisolone reduced from 2 mg/kg to to 1 mg/kg in first month, to 0.5/kg/day in second month, and 0.25 mg/kg/day in third month; Azathioprine reduced from 2 mg/kg/day to 1.6 mg/kg/day in second months, completed elimination after 5 months | from 26% to 47% |

[1]Diagnosis of IMHA was performed by reticulocyte count, Spherocyte (Blood smear), Coomb's test, or bone marrow examination.
[2]One capsules, 400 mg, 1 billion viable cells of P. acidilactici and S. boulardii was fed to the dogs with IMHA
[3]dog was fed with two capsules, 800 mg, 2 billion viable cells of P. acidilactici and S. boulardii per day.
[4]Packed Cell Volume (PCV) is the standard protocol to measure the amount of blood cells of animals.

Table 3 shows the effect of treatment with probiotics comprised of P. acidilactici and S. boulardii on the amount of steroid Prednisolone and immune suppressors cyclosporine or azathioprine required to treat dogs afflicted with IMHA. In all cases the level of steroid and immune suppressor required was reduced. In three cases the immune suppressor was eliminated. In all cases the health of the animals improved, as indicated by substantial increases in packed cell volume, with low packed cell volume an indicator of IMHA.

IBD and NEP Treatment

Diagnosis of animals with IBD or NEP. IBD diagnosis requires ruling out all other possible causes for chronic intestinal inflammation, as well as confirmation by the presence of excess inflammatory cells in the GI tract (Omi et al., 2008). Several diagnostic tests were run: 1) history of suffering from chronic digestive disorders such as vomiting, diarrhea, loss of appetite, or weight loss over an extended period of time, 2) fecal sample analysis, blood analysis, and the application of antibiotic treatment to eliminate pathogen or parasite infections, 3) either biopsy or endoscope for pathological analysis of the inflammatory cells on the surface of the GI tracts. For patients diagnosed as IBD all three above diagnostic procedures were used. For patients diagnosed as NEP, only the first two diagnostic procedures were used, or the history of digestive disorders was less than three weeks.

Table 2 summarizes the results of further administrating probiotics P. acidilactici and S. boulardii along with prednisolone and immune suppressors to cats and dogs with chronic diseases.

TABLE 2

| Line | Disease | Number of Total cases | Number with reduction of prednisolone and/or immune suppressors | Number terminating prednisolone and/or immune suppressors |
|---|---|---|---|---|
| 1 | IBD | 6 | 5 | 2 |
| 2 | NEP# | 6* | 3 | 1 |
| 3 | IMHA | 7** | 6 | 1 |
| 4 | total | 19 | 14 | 4 |

Dogs with chronic digestive disorders involving microbial assays, blood tests, and treatment with antibiotics to eliminate bacterial or parasitic infection, but not confirmed by biopsy analysis.
*Two cases without prednisolone or immune suppressors and one with no report on reduction of prednisolone or immune suppressors.
**One case of a cat with IMHA and panreatitis showed no reduction of prednisolone. With treatment with probiotics P. acidilactici and S. boulardii the dog became free of diarrhea and vomiting and had a good appetite.

Line 1 summarizes the treatment of two cats and four dogs with IBD with prednisolone and immune suppressors as well as probiotics P. acidilactici and S. boulardii performed in six animal hospitals in Japan and the USA according to the protocols in FIGS. 2A and 2B. Except for one dog with IBD, all five IBD dogs and cats had results with probiotics P. acidilactici and S. boulardii which allowed reducing dosage of prednisolone. Within these 5 dogs and cats, one dog was able to eliminate prednisolone treatment completely as did one cat. One dog with IBD was only administered daily probiotics P. acidilactici and S. boulardii only after metronidizole treatment was completed. In this animal the digestive system was significantly improved. One dog diagnosed with mild IBD did not respond well when treated with Enterococcus based probiotics. After administration of P. acidilactici and S. boulardii the dog had significant improvement.

Line 2 summarizes the effects of treatment of animals with nonspecific enteropathies (henceforth NEP) with prednisolone and/or immune suppressors. When cats and dogs suffer from chronic digestive disorders the possibilities of bacterial or parasite infection were excluded by extensive examination of fecal analysis, blood tests, and antibiotics treatments. However, pathological confirmations by biopsy analysis were not performed and these cats and dogs were described to have NEP. In six animals diagnosed as NEP, two cases were treated with a once daily P. acidilactici and S. boulardii probiotics capsule after antibiotics treatment was completed, and the digestive disorders were controlled successfully. In four cases a once daily P. acidilactici and S. boulardii capsule was administrated along with prednisolone and/or immune suppressors. Of these four cases, three cases clearly showed the reduction of prednisolone dosages, and in one case it was possible to eliminate prednisolone treatment.

Line 3 summarizes the treatment of seven dogs with IMHA with probiotics P. acidilactici and S. boulardii and with prednisolone and immune suppressors following the protocol of FIGS. 2A and 2B. Six dogs clearly showed significant improvement in PCV results after reduced dosages of prednisolone and immune suppressors but with maintained probiotic treatment.

Line 4 is the summary of all 19 chronic cases which included animals with IBD, NEP, and IMHA. The administration of P. acidilactici and S. boulardii probiotics together with steroids and/or immune suppressors made possible the reduction of steroid and immune suppressors dosages in long term applications. In four cases it was possible to eliminate steroids and/or immune suppressors without any relapses.

In summary, the addition of probiotics *P. acidilactici* and *S. boulardii* into the conventional IBD treatment allowed for complete termination of antibiotic treatment in two IBD dogs and one NEP cat and in two NEP dogs. Conventional antibiotic treatment in one NEP cat was successfully terminated.

Addition of probiotics *P. acidilactici* and *S. boulardii* allowed successful reduction of prednisolone dosage in two IBD cats and one IBD dog and one NEP dog. Prednisolone and antibiotic administration was completely terminated in one NEP dog with probiotics *P. acidilactici* and *S. boulardii*.

Bloody diarrhea in one NEP cat was successfully treated with probiotics *P. acidilactici* and *S. boulardii* and diet changes for six months without use of any prescription drugs.

These results showed that administering probiotics *P. acidilactici* and *S. boulardii* to IBD or NEP dogs or cats was without negative effects and helped to reduce or to terminate conventional drug treatment, such as Prednisolone or antibiotics.

TABLE 3

Treatment of dogs with IBD or dogs with NPE by MITOMAXSUPER ™ only

| Pets | Diseases[1] | Symptom before treatment | Symptom after treatment[2] |
|---|---|---|---|
| 9 year, 9 month old miniature dachshund | IBD | Frequent loose stool, bloody diarrhea | After changed diet to food decomposed excess water and fed with MITOMAXSUPER ™, stool became normal and steady for 3 months |
| 10 years old mix cat | NPE | Bloody diarrhea | After 5 days treatment, diarrhea stop, and the stool became normal for 6 months |
| 8 years, 5 months old Welsh Corgi | NPE | Vomiting, diarrhea, lose appetite | After three days treatment, vomiting stop, Stool became normal, and appetite became normal. Continuing to apply MITOMAXSUPER ™ for 10 months without remission |

MITOMAXSUPER ™ means a probiotic capsule containing 400 mg of one billion live dried mixtures of *P. acidilactici* and *S. boulardii*.

The results shown in Table 3 show that a cat and dog with NPE, and a dog with IBD had symptoms relieved by treatment with a capsule of a probiotic comprising of *P. acidilactici* and *S. boulardii*.

TABLE 4

Effects of MITOMAXSUPER ™ on dogs with Atopic Dermatitis

| | Significant Improvement* | Good Improvement | No Improvement |
|---|---|---|---|
| Number of dogs with Atopic Dermatitis | 14 | 3 | 6 |
| % of dogs | 60.8% | 13.1% | 26.1% |

*dogs diagnosed to have atopic dermatitis were treated with MITOMAXSUPER ™ based on body weight:
<5 kg: 2 capsules, 2 billion live dried mixtures of *P. acidilactici* and *S. boulardii*
5-15 kg: 4 capsules, 4 billion live dried mixtures of *P. acidilactici* and *S. boulardii*
15-35 kg: 6 capsules, 6 billion live dried mixtures of *P. acidilactici* and *S. boulardii*
>35 kg: 8 capsules, 8 billion live dried mixtures of *P. acidilactici* and *S. boulardii*

Table 4 shows the effect of treatment of dogs with atopic dermatitis with probiotics *Pediococcus acidilactici* and *Saccharomyces boulardii*. The results indicated most dogs were helped by such treatment with 60.8% showing significant improvement; 13.1% showing good improvement; and 26.1% showing no improvement.

SUMMARY

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope. The applicant or applicants have attempted to disclose all the embodiments of the invention that could be reasonably foreseen. There may be unforeseeable insubstantial modifications that remain as equivalents.

What is claimed is:

1. A method for treating a disorder selected from the group consisting of inflammatory bowel disorder (IBD) and nonspecific enteropathy (NEP) comprising:
   (a) identifying a human, feline or canine subject in need of treatment for said disorder;
   (b) initiating treatment of said subject with an effective amount of cyclosporine and/or azathioprine;
   (c) initiating probiotic treatment of said subject with an effective amount of *Pediococcus acidilactici* and *Saccharomyces boulardii*;
   (d) reducing a dosage of said cyclosporine and/or azathioprine subsequent to initiation of said probiotic treatment.

2. A method according to claim 1, wherein said reducing a dosage comprises reducing a dosage of at least one of cyclosporine and/or azathioprine to zero.

3. A method according to claim 2, wherein said reducing a dosage comprises reducing a dosage of cyclosporine and azathioprine to zero.

4. A method according to claim 1, comprising ceasing treatment with said cyclosporine and/or azathioprine while continuing said probiotic treatment.

5. A method for treating a disorder selected from the group consisting of inflammatory bowel disorder (IBD) and nonspecific enteropathy (NEP) comprising:
   (a) identifying a human, feline or canine subject in need of treatment for said disorder;
   (b) initiating treatment of said subject with an effective amount of prednisolone or prednisone;
   (c) initiating probiotic treatment of said subject with an effective amount of *Pediococcus acidilactici* and *Saccharomyces boulardii*;
   (d) reducing a dosage of said prednisolone or prednisone subsequent to initiation of said probiotic treatment.

6. A method according to claim 5, wherein said reducing a dosage comprises reducing a dosage of said prednisolone or prednisone to zero.

7. A method according to claim 5, comprising ceasing treatment with said prednisolone or prednisone while continuing said probiotic treatment.

8. A method for treating a disorder selected from the group consisting of inflammatory bowel disorder (IBD) and nonspecific enteropathy (NEP) comprising:
   (a) identifying a human, feline or canine subject in need of treatment for said disorder;
   (b) initiating treatment of said subject with an effective amount of at least one member of the group consisting of cyclosporine, azathioprine and prednisolone or prednisone;
   (c) initiating a probiotic treatment of said subject with an effective amount of *Pediococcus acidilactici* and *Saccharomyces boulardii*;
   (d) reducing a dosage of at least one of said at least one member of the group consisting of cyclosporine, azathioprine and prednisolone or prednisone subsequent to initiation of said probiotic treatment.

9. A method according to claim 8, wherein said reducing a dosage comprises reducing a dosage of at least one of said at least one member of the group consisting of cyclosporine, azathioprine and prednisolone or prednisone to zero.

10. A method according to claim 9, wherein said reducing a dosage comprises reducing a dosage of at least two of said at least one member of the group consisting of cyclosporine, azathioprine and prednisolone or prednisone to zero.

11. A method according to claim 8, comprising ceasing treatment with all of said at least one member of the group consisting of cyclosporine, azathioprine and prednisolone or prednisone while continuing said probiotic treatment.

12. A method according to claim 8, wherein said initiating treatment of said subject with at least one member of the group consisting of cyclosporine, azathioprine and prednisolone comprises initiation of treatment with cyclosporine and/or azathioprine and also with prednisolone or prednisone.

* * * * *